United States Patent [19]

Townsend et al.

[11] Patent Number: 5,658,244

[45] Date of Patent: Aug. 19, 1997

[54] KNEE ORTHOSIS WITH IMPROVED SUSPENSION STRAP

[76] Inventors: Jeffrey Townsend, 7106 Crestwood St., Bakersfield, Calif. 93304; Larry Reib, 5900 Coyle Ave., Carmichael, Calif. 95608

[21] Appl. No.: 568,338

[22] Filed: Dec. 6, 1995

[51] Int. Cl.⁶ ........................................ A61F 5/00
[52] U.S. Cl. ................................. 602/26; 602/23
[58] Field of Search ..................... 602/5, 16, 23, 602/26

[56] References Cited

U.S. PATENT DOCUMENTS

| | | | |
|---|---|---|---|
| 4,506,661 | 3/1985 | Foster | 602/26 |
| 4,802,466 | 2/1989 | Meyers et al. | 602/26 |
| 4,854,308 | 8/1989 | Drillio | 602/26 X |
| 4,940,045 | 7/1990 | Cromartie | 602/26 X |
| 4,966,133 | 10/1990 | Kausek | 602/26 X |
| 4,986,264 | 1/1991 | Miller | 602/26 X |
| 4,991,571 | 2/1991 | Kausek | 602/26 X |
| 5,458,565 | 10/1995 | Tillinghast, III et al. | 602/26 |

*Primary Examiner*—Linda C. Dvorak

[57] ABSTRACT

A knee orthosis is provided which includes a suspension strap for securing the orthopedic device to the wearer's leg. The suspension strap includes a band portion that traverses the inner sides of tibial struts and is connected to the medial side tibial strut at point of connection that is lower than a point of connection of the band portion to the lateral side tibial strut. This positioning provides enhanced suspension and support by maximizing the contact area between the suspension strap and the wearer's leg, and provides an advantageous antero-posterior directed force, without compressing the peroneal nerve in the wearer's leg. In addition, a pre-formed spacer may be utilized to aid in providing the antero-posterior directed force and enhancing overall support and suspension.

15 Claims, 8 Drawing Sheets

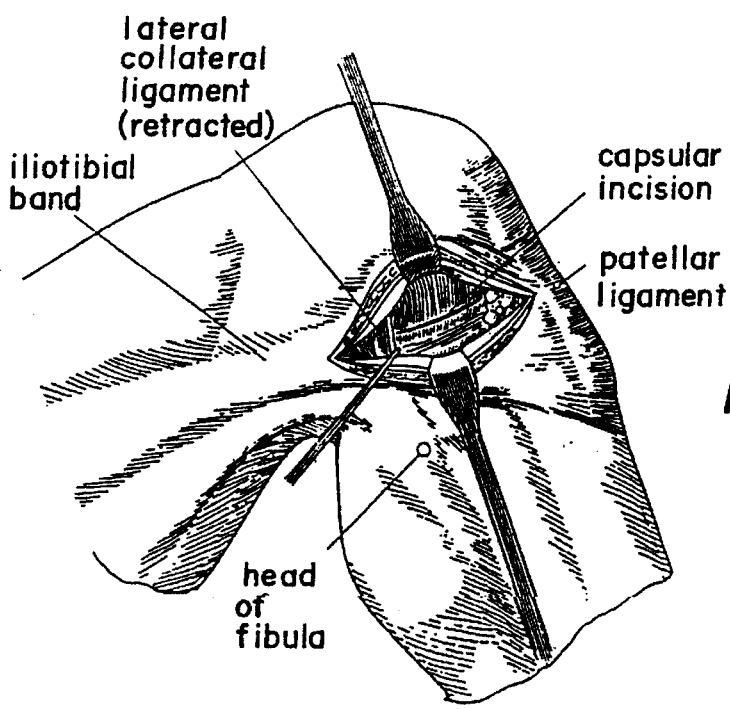
FIG. 6A
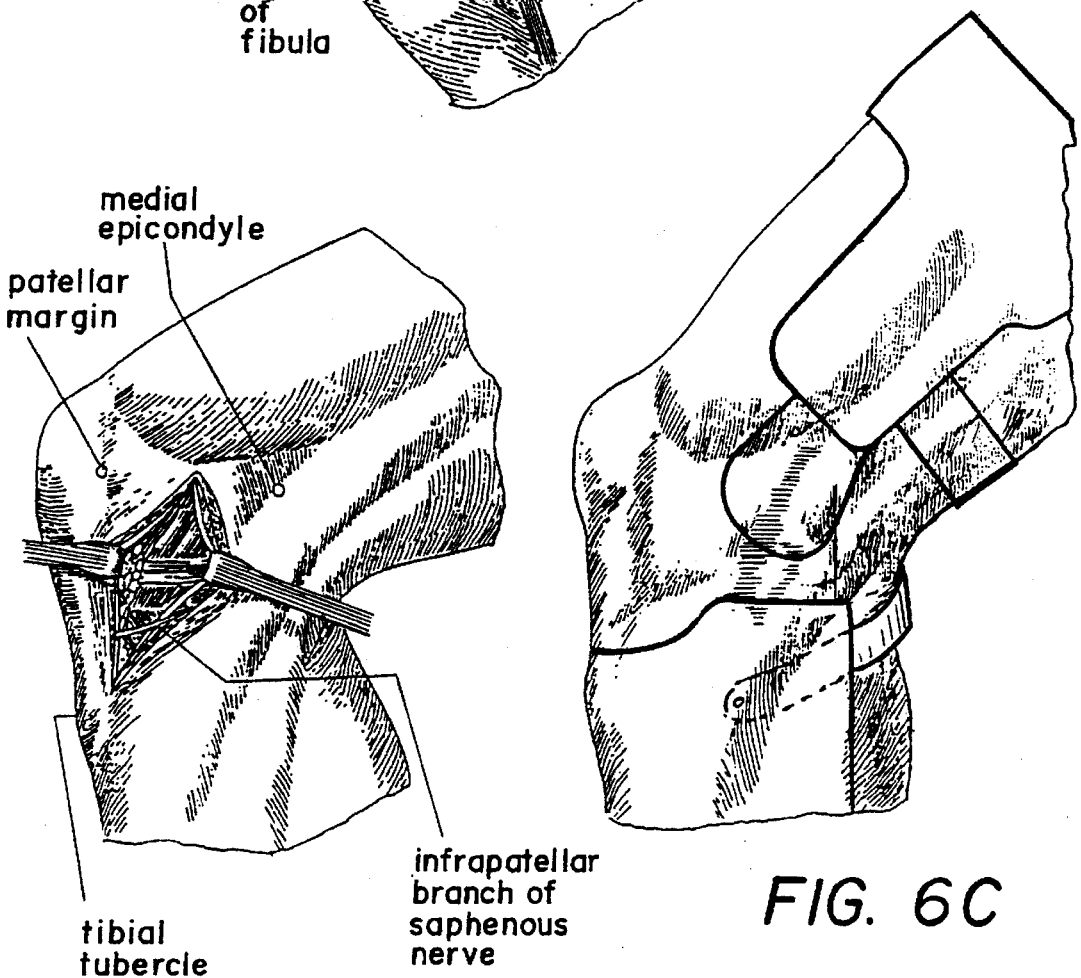
FIG. 6B
FIG. 6C 5,658,244

KNEE ORTHOSIS WITH IMPROVED SUSPENSION STRAP

BACKGROUND OF THE INVENTION

1. Field of the Invention

This invention relates to orthopedic devices for individuals whose bones have been weakened by injury and support and stabilization of the bones is necessary. In particular, the present invention relates to a suspension strap for a knee orthosis that provides optimum support and suspension by maximizing the contact area between the orthosis and the wearer's body.

2. Description of Related Art

A conventional orthopedic knee brace is shown in U.S. Pat. No. 5,415,625 to Cassford et at. The knee brace includes rigid upper and lower cross members, and includes upper and lower medial and lateral arms (or struts) that are connected by hinges, thereby permitting pivotal movement of the knee. In addition, attachment straps are used to secure the brace to the leg of the user together with cross members running between the lateral and medial struts. It should be noted that while Cassford et al. appears to disclose an "off-the-shelf" type of a knee brace, where the support elements are not formed to fit a particular user's leg, conventional knee braces may also be of a custom made design, where shell-type support members are molded to conform to the shape of the specific wearer's leg.

The Cassford et al. design provides inflatable pads mounted on the struts for adjusting the fit of the brace to a particular user or for a particular activity. The inflatable pads, however, suffer from the problem that one must continuously monitor the pads and inflate/deflate them as necessary using independent fluid injecting devices. In addition, the inflatable pads can cause an offset of the intended contact area between the attachment straps and the person's leg, which may lead to unsatisfactory support from the attachment straps. In extreme situations, this problem may cause unintended areas of the person's leg to be compressed, resulting in dangerous pressure on nerves in the leg.

The attachment straps in the Cassford et al. design are positioned in a conventional fashion, traversing on the outside of the orthosis from the medial to lateral struts, with attachment points on the outside of the struts or shells. This positioning of the attachment straps, however, has drawbacks. By having the attachment points on the outside of the strut or shell, a decreased surface area of the attachment strap contacts the wearer's skin which, in turn, decreases the amount of direct support provided by the straps, particularly the calf suspension strap. In addition to this decreased area of support, having the attachment straps attached in this fashion causes an inward tightening of the brace in a medial-lateral fashion. This tightening is disadvantageous because it results in the hinge pads being unduly forced against the knee joint. In addition, the tightening may cause the struts to be misangled relative to the person's leg.

U.S. Pat. No. 4,633,867 to Kausek et al. discloses a knee brace that includes a flexible, elastic popliteal strap that extends in a substantially horizontal plane around the back of the upper calf. The popliteal strap, however, is only used for compressing a shin plate against the leg and prohibits excessive rotation or misalignment of the shin plate. The popliteal strap is elastic and flexible, and therefore does not provide any firm support or stabilization of the knee that a calf suspension strap provides. In addition, this strap attaches to the outside of the shin plate or shell, and therefore it does not provide the maximum contact area possible between the strap and the wearer's body. Furthermore, having the strap aligned in a horizontal fashion, perpendicular to the wearer's leg, results in the possible risk that the strap is directed towards the critical area of a peroneal nerve which is located at the neck of the fibula. The strap's line of action is directly over the neck of the fibula, creating a distinct risk of compressing the peroneal nerve. It should be noted that the conventional attachment of the attachment straps, as disclosed in Cassford et al., avoided this problem of placing pressure on the peroneal nerve by attaching the attachment straps on the outside of the orthosis shell. Such designs avoid pressure on the nerve because the calf strap does not place pressure on the fibular neck, an area where the nerve crosses close to the surface of the skin. However, in the Cassford et al. design, this advantage may be negated due to the inflatable pads causing a repositioning of the attachment straps, as discussed above.

Other conventional designs for knee braces are disclosed in U.S. Pat. No. 5,092,030 to Maurer, U.S. Pat. No. 4,732,143 to Kausek et al., and U.S. Pat. No. 4,312,335 to Daniell, Jr. The above-discussed problems with the prior art indicate that the need exists for a knee orthosis in which maximum contact area between the calf suspension strap and the wearer's leg can be obtained without the risk of damaging nerves in the leg.

SUMMARY OF THE INVENTION

It is an object of the present invention to overcome the disadvantages of the prior art and to provide a knee orthosis having suspension straps that provide the maximum support for the orthosis on a wearer's leg without painful or damaging pressure being applied to nerves of the leg, particularly the peroneal nerve.

It is another object of the present invention to provide a knee orthosis having a suspension strap that enhances the fit and function of the knee orthosis by optimizing suspension.

It is yet a further object of the present invention to provide a knee orthosis having a suspension strap that maximizes the contact area between the suspension strap and the wearer's leg to maximize support and suspension for the orthosis on the leg.

It is still another object of the present invention to provide a knee orthosis having a suspension strap positioned so as to maximize the contact area between the suspension strap and the wearer's leg without causing discomfort to the wearer's muscles in the area of the suspension strap.

These and other objects that will become apparent in the following description are achieved in accordance with preferred embodiments of the invention. In particular, a knee orthosis is provided having lower and upper support portions, each including struts for stabilizing the upper and lower parts of the leg relative to the knee, a joint mechanism for connecting the upper and lower support portions and to permit controlled pivotal movement of the wearer's leg, and a suspension strap that traverses the inside of the struts of the knee orthosis and across the leg, such that the suspension strap is lower on a medial side of the leg than on the lateral side of the wearer's leg, in a manner following the natural contour of the leg.

Furthermore, a pre-formed spacer may be used, positioned directly adjacent the struts to further secure the contact area between the suspension straps and the wearer's leg, to provide an antero-posterior (front-to-back) directed force of the suspension strap relative to the wearer's leg. The suspension strap can be used with both custom made and "off-the-shelf" model knee orthoses.

These and further objects, features and advantages of the present invention will become apparent from the following description when taken in connection with the accompanying drawings which, for purposes of illustration only, show several embodiments in accordance with the present invention.

BRIEF DESCRIPTION OF THE DRAWINGS

FIGS. 6a and 6b are diagrams of lateral and medial sides, respectively of a right leg and FIG. 6c is a medial side view diagram for explaining positioning of an upper tibial suspension strap in accordance with the invention;

DETAILED DESCRIPTION OF THE PREFERRED EMBODIMENTS

Figure 1:
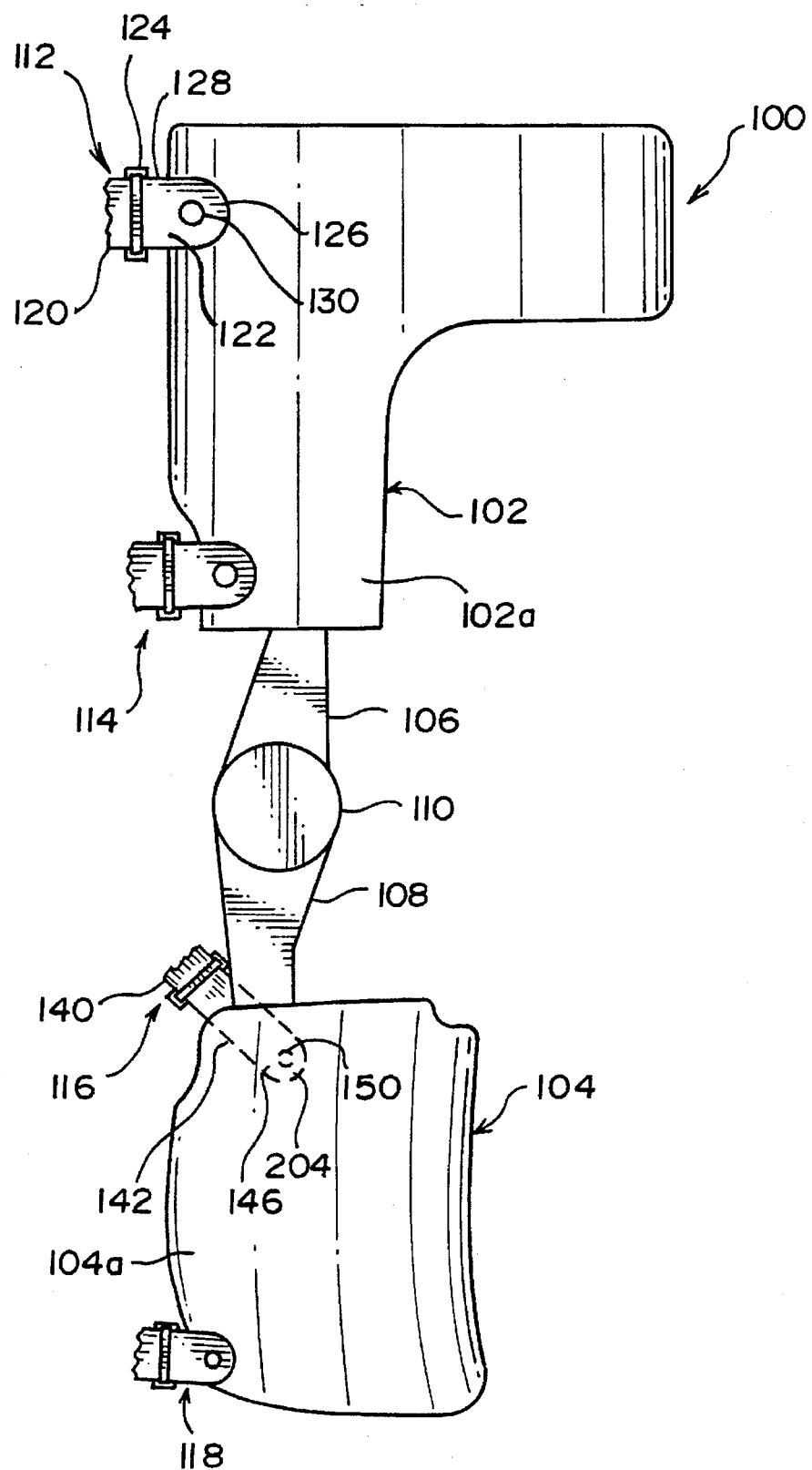
FIG. 1 is a schematic of a side view of a knee orthosis in accordance with a first embodiment of the present invention.

FIG. 1 illustrates generally a knee orthosis 100 of the custom made type in which an upper support shell 102 and a lower support shell 104 have been custom-molded to provide a form-fitting contour that has been individualized to match the shape of a particular wearer's leg. It should be noted that other shapes of support shells, and additional support shells, may be used depending on a particular situation, such as when additional/different support is necessary. The support shells have side portions 102a, 104a to which a femoral strut 106 or a tibial strut 108 is attached at each of medial and lateral sides of the orthosis 100, the side portions 102a, 104a being connected at the front of the orthosis by either a cross member 102b which is local to only the top part of the side portions, or by a cross member 104b which extends over substantially the full height of the side portions.

The struts 106, 108 support the upper and lower parts of the wearer's leg, and are generally made of a rigid material, such as aluminum, titanium, or fiber and resin composites. The femoral struts 106 are hinged to the tibial struts 108 by a joint mechanism 110. The details of joint mechanism 110 are not depicted, since any conventional joint mechanism that permits swinging movement of the struts relative to each other may be utilized. However, a preferred joint mechanism is that which forms the subject of one of the present applicant's U.S. Pat. No. 5,259,832, the contents of which are incorporated herein by reference to the extent necessary to complete an understanding of this invention.

The knee orthosis 100 further includes a number of attachment straps 112, 114, 116, 118. As shown in FIG. 1, two of the attachment straps 112, 114 are connected between the leg portions 102a of the upper support shell 102 and two of the attachment straps 116, 118 are connected between leg portions 104a of the lower support shell 104. While various attachment devices may be used to attach the attachment straps to the support shells, and the attachment straps may be variously constructed, a preferred construction for the attachment straps as well as a particularly suitable form of attachment will now be described relative to attachment strap 112.

Attachment strap 112 has a first band portion 120 and a second band portion 122. One end 126 of second band portion 122 is permanently attached to one side (e.g., the lateral side shown here) of the upper support shell 102 through the use of a metal rivet 130. A ring 124 is attached to the other end 128 of second band portion 122. A first end of the first band portion 120 is permanently attached to the other side (e.g., the medial side, shown in FIG. 4) of upper support shell 102 using a rivet similar to rivet 130. The second end of first band portion 120 traverses around the rear of the wearer's leg, through ring 124 and is then attached to first band portion 120 using, for example, a Velcro®, hook and loop type fabric attachment means (not shown), one part of which (e.g., the hook fabric part) is disposed on the second end of the first band portion and the other part (e.g., the loop fabric part) is secured on the first band portion in an area that is located between ring 124 and the first end. The attachment straps, themselves, are generally made of a fabric material, which is inelastic, and may include foam or other padding so as to be comfortable against the wearer's leg.

It is noted that the calf suspension strap 116, like the other attachment straps, is connected in a similar manner as attachment strap 112, but in this case, to lower support shell 104. However, the positioning of suspension strap 116 is different from that of the other attachment straps and is very important. This positioning will now be described in detail in relation to FIGS. 1-6 in connection with the custom made model knee orthosis 100 of FIG. 1, and any necessary differences in the case of an off-the-shelf model will be described later on, below. As shown in FIG. 1, a first end 146 of a second band portion 142 of suspension strap 116 is connected at the inner side of the lower support shell 104, e.g., using rivet 150, at a point that is further forward than the attachment points of the suspension straps 112, 114, 118. Furthermore, suspension strap 116 passes along the inner side of the tibial struts 108 from its point of connection on the inner side of lower support shell 104. This connection of the suspension strap 116 under support shell 104 serves to maximize the contact area between the suspension strap 116 and the wearer's leg.

Figure 2:
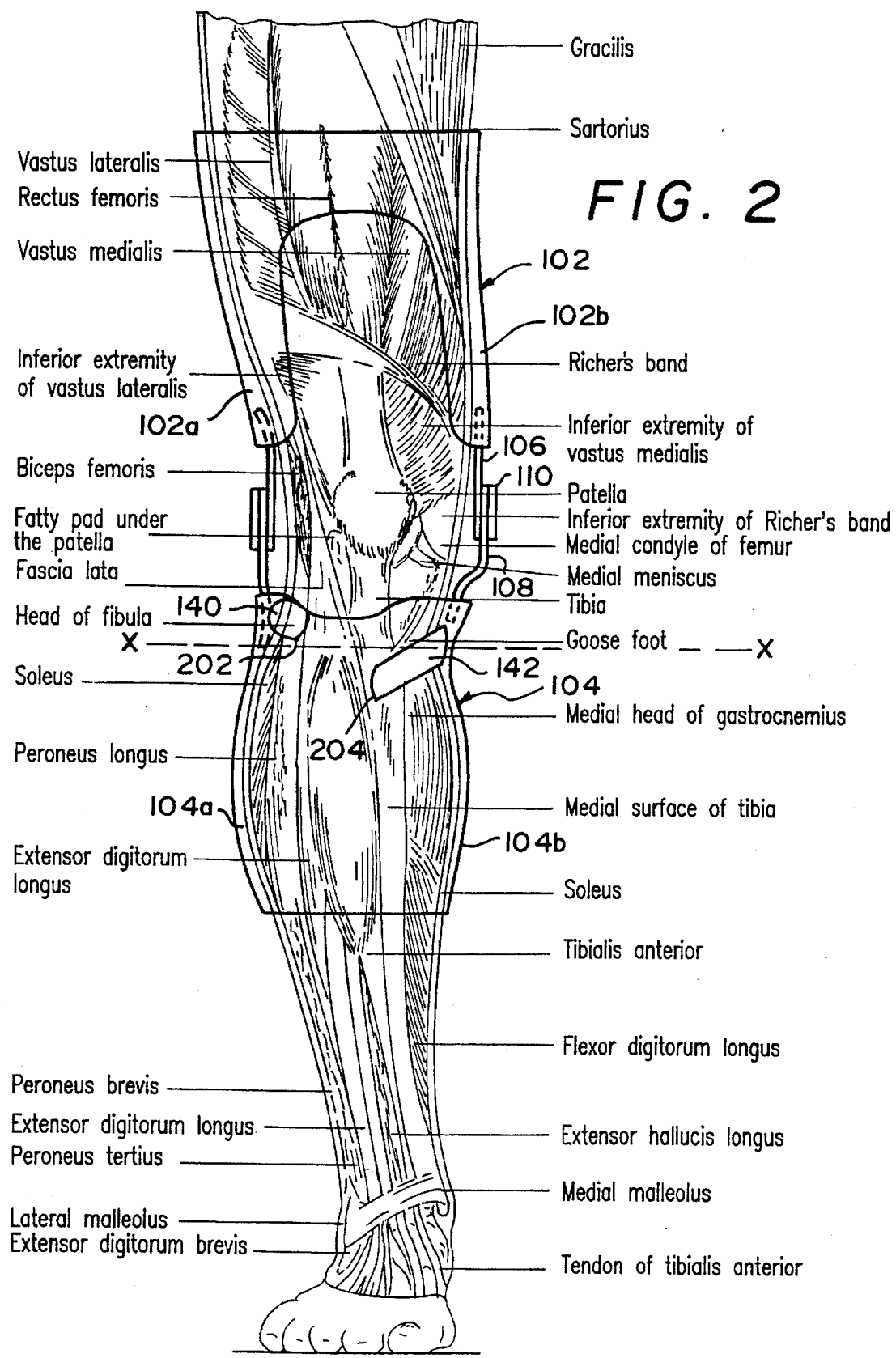
FIGS. 2-5 are, respectively, anterior, posterior medial and lateral anatomical views of a right leg for explaining positioning of the knee orthosis relative to the muscles of the leg in accordance with the first embodiment of the present invention.
Figure 3:
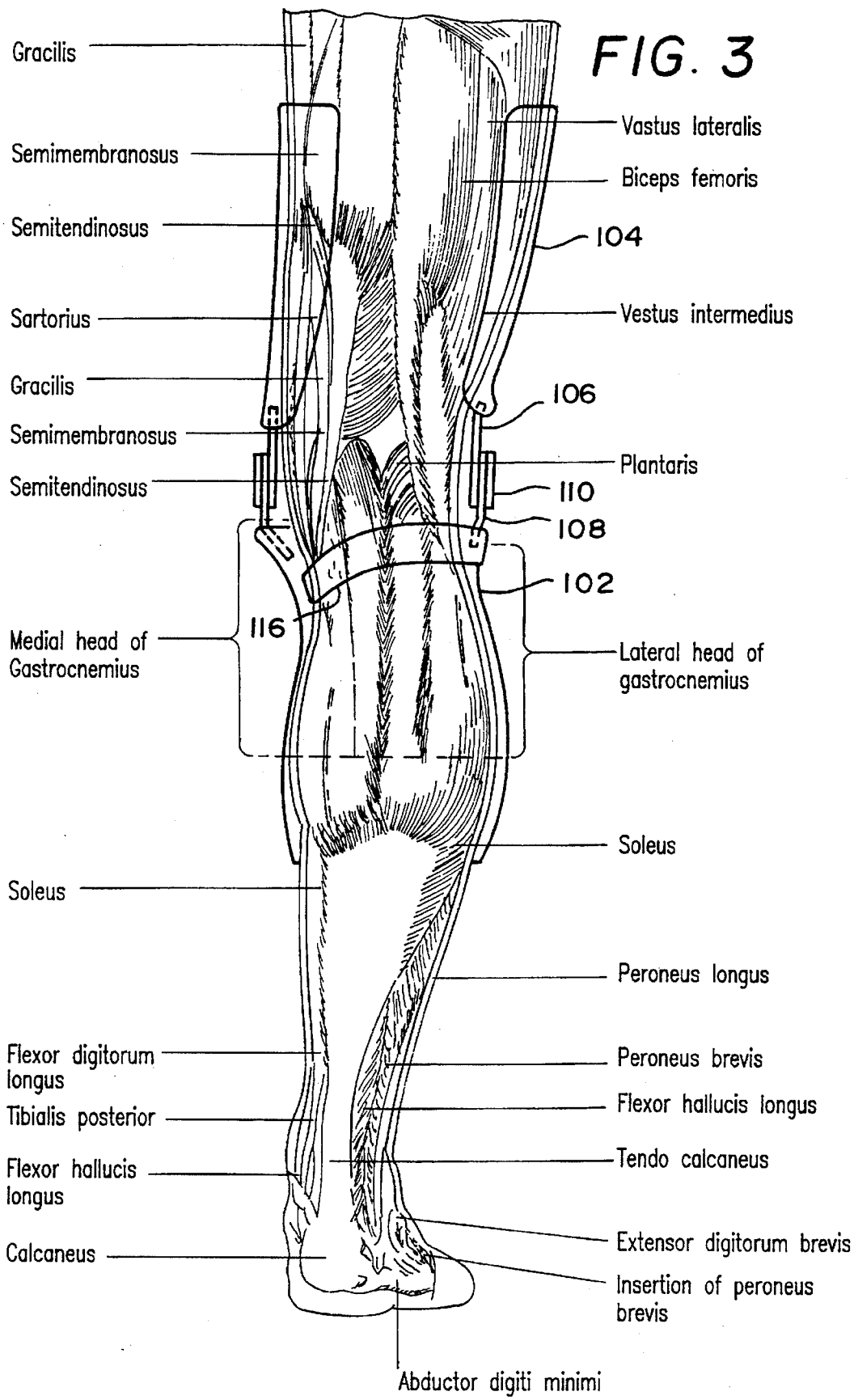
Figure 4:
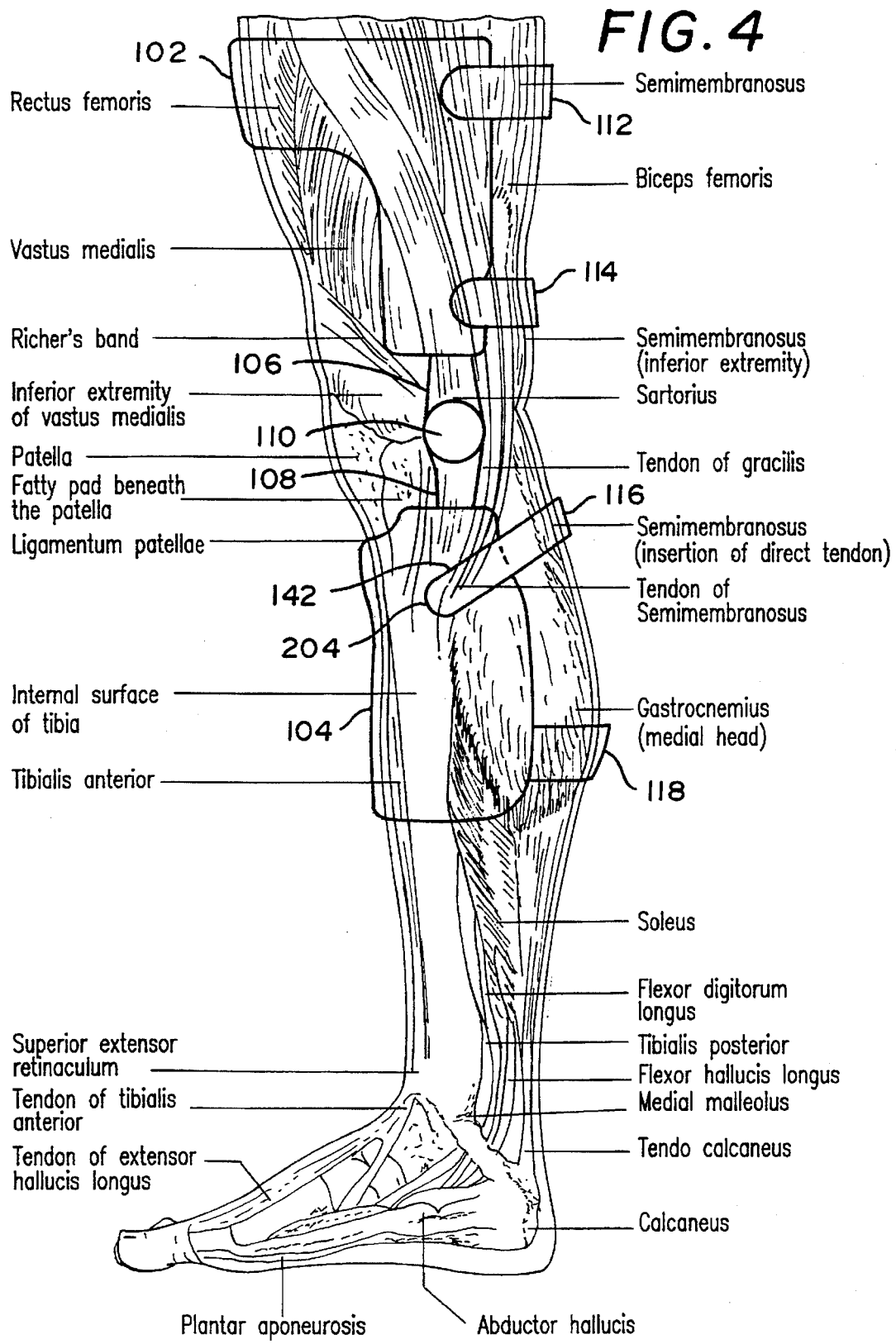
Figure 5:
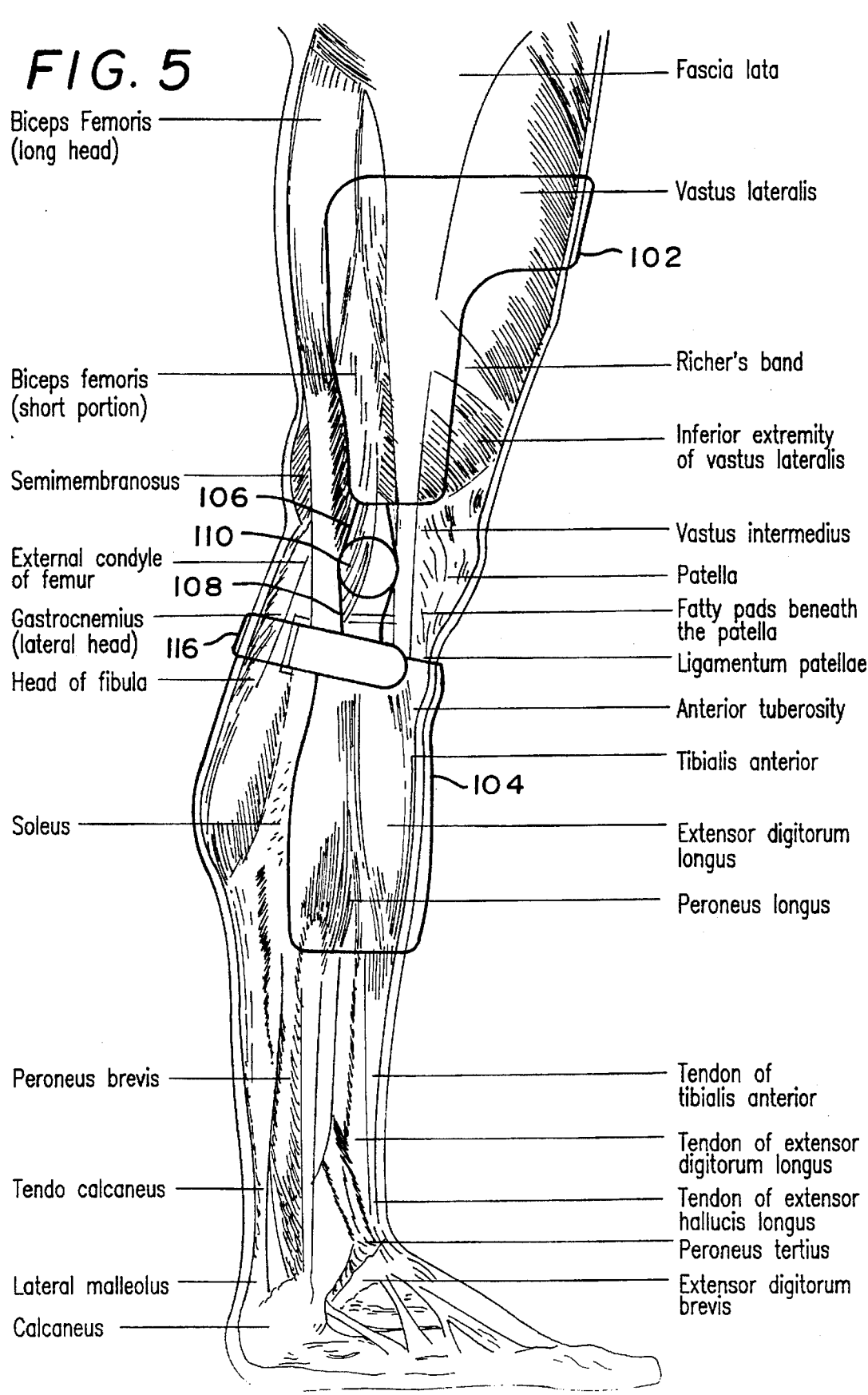

In addition, as shown in FIG. 2, an end 202 of a first band portion 140 of the suspension strap 116 is connected higher on the lower support shell 104 (i.e., closer to joint mechanism 110) than is an end 204 of a second band portion 142, as shown relative to horizontal axis x in FIG. 2. In other words, the connection of suspension strap 116 is lower on the medial side of the wearer's leg than on the lateral side. As shown in FIGS. 3-5, this results in suspension strap 116 following the natural contour of the muscles of the wearer's leg.

Numerous advantages are associated with the above-described positioning of suspension strap 116. First, by positioning suspension strap 116 on the inside of the tibial struts 108, attaching the suspension strap 116 at the inside of the lower support shell 104, and attaching the strap further inward on the lower support shell 104, a maximum contact area is produced between the suspension strap and the wearer's calf. This positioning provides optimum support and stabilization, including greater hyperextension control, compared to conventional designs. Second, this positioning achieves a redirection of the force vector of the suspension strap 116 into a more advantageous antero-posterior direction. Conventional positioning of suspension straps on the outside of the orthosis tend to tighten the knee orthosis in a medial-lateral dimension, which causes unnecessary force against the knee joint where the orthosis contacts the knee. Furthermore, the line of force of such suspension straps is across the calf and applies insufficient force against the leg, thereby permitting the suspension strap to displace down over the calf during movement of the leg. This results in insufficient support and suspension of the knee orthosis, and may even cause the suspension strap to locate against the fibular neck in the calf, which causes problems discussed below.

Instead, in the present invention, redirecting the force of suspension strap 116 into an antero-posterior force direction provides a force directed against the calf, such that the suspension strap 116 will not displace downward over the calf itself, thereby allowing unexpectedly firm suspension of the knee orthosis and avoiding the potential problem of placing too much pressure against the fibular neck. This limitation of pressure against the fibular neck is another advantageous feature of the suspension strap positioning of the present invention in that it avoids impingement upon the peroneal nerve that is located at the neck of the fibula. If the strap were positioned in a horizontal fashion, directly perpendicular to the leg, the suspension strap would have a line of action directly over the neck of the fibula, where the nerve crosses close to the surface of the skin, and a distinct risk of compressing the nerve would be present as a result. By contrast, by positioning of suspension strap 116 higher on the lateral side than on the medial side, along the natural contour of the person's leg, this impingement is avoided because the strap does not direct any significant force directly against the fibular neck. The suspension strap 116 remains above the apex of the calf, which is especially important in light of the antero-posterior vector that directs the suspension strap against the calf. If the suspension strap were to traverse down over the fibular neck, this antero-posterior force vector may become detrimental. Fourth, the positioning of the suspension strap 116 is such as to relieve the medial hamstrings, which are especially prominent when the wearer is in a seated position. Yet a fifth advantage, as shown in FIGS. 6a and 6b, is that the line of action taken by suspension strap 116 follows the natural curve of the flexion fold 600 on the posterior aspect of the wearer's leg. This, among other things, provides greater comfort to the wearer.

Figure 7:
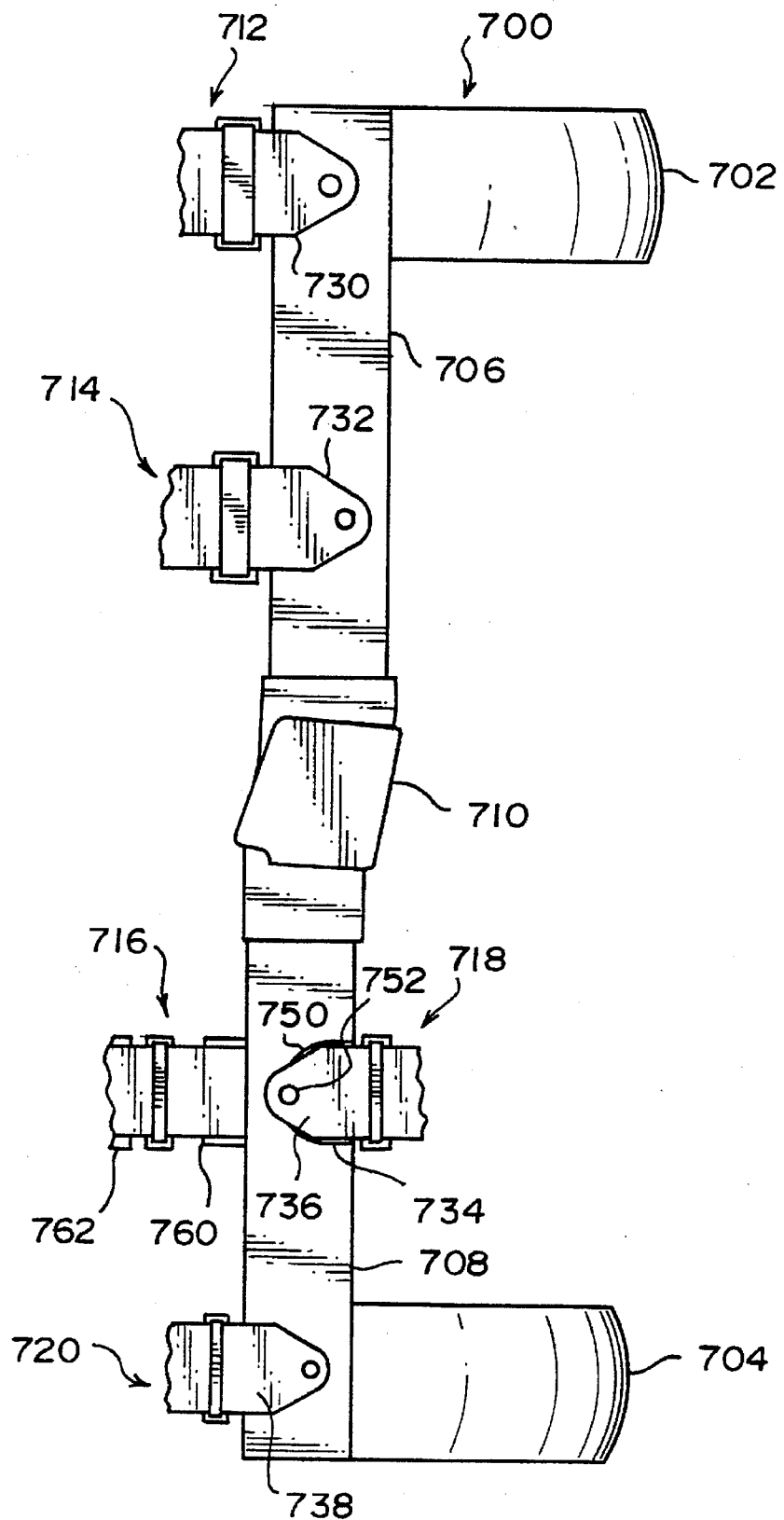
FIG. 7 is a schematic side view of a knee orthosis in accordance with a second embodiment of the present invention.
Figure 8:
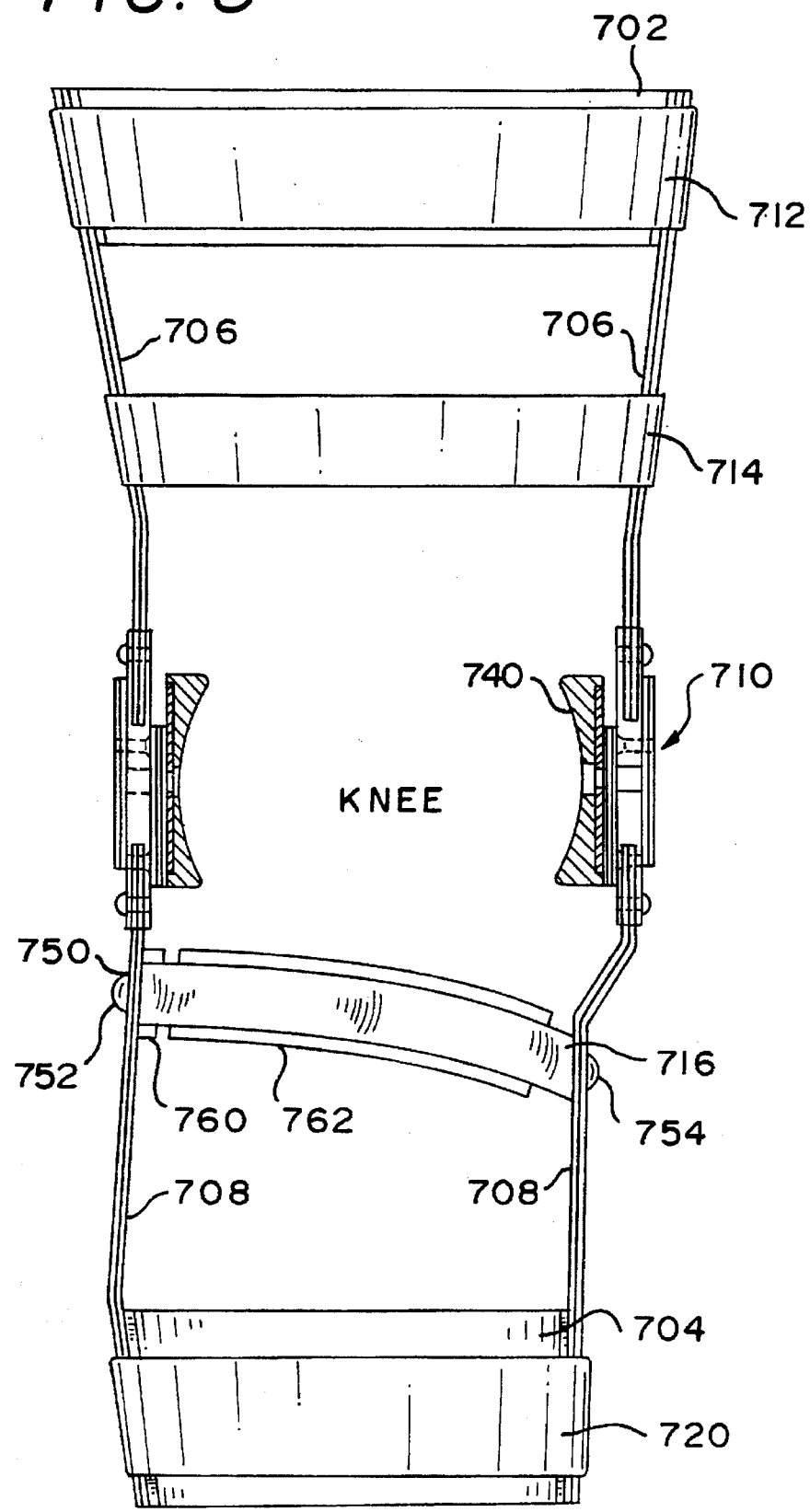
FIG. 8 is a rear view of a knee orthosis in accordance with the second embodiment of the present invention.

Referring now to FIGS. 7–8, a suspension strap in accordance with a second preferred embodiment of the present invention will be described. This embodiment relates to an off-the-shelf type model knee orthosis 700 which is of a generic size and shape as opposed to being designed for a specific individual. The off-the-shelf knee orthosis 700 is very similar to the custom made knee orthosis 100 described above with resect to FIGS. 1–5, including suspension straps 712, 714, 717, 718, 720, connections for the suspension straps 730, 732, 734, 737, 738, and joint mechanism 710 (including pads 740). In the present embodiment, however, the femoral struts 706 and tibial struts 708, together, extend the entire length of the knee orthosis, while this may not necessarily be true with the custom made model 100 having upper and lower support shells 102,104 (see, FIG. 1). That is, instead of the upper and lower support shells that are custom-molded to a particular user's leg, an upper support bar 702 and a lower support bar 704 are utilized as the frontal cross members connecting the femoral and tibial struts, respectively.

The suspension strap 716, as compared to the suspension strap 116 of the FIG. 1 embodiment, cannot be attached to a lower support shell, further inward than the remaining suspension straps 712, 714, 718, 720. Instead, suspension strap 716 must be attached somewhere on tibial strut 708, itself. In this regard, the suspension strap 716 has a first end 750 that attaches on the outside of shut 708, then traverses around the front edge of tibial shut 708, such that the main band portion of the suspension strap 716 remains between the medial and lateral struts 708, thereby maximizing the contact area between the suspension strap and the wearer's leg.

Referring now specifically to FIG. 8, in addition to having the suspension strap 716 traverse the inner sides of tibial struts 708, the medial side attachment point 754 for the suspension strap is lower than the lateral side attachment point 752 for the strap. This positioning of suspension strap 716 provides many of the advantages noted above in connection with the first embodiment. As refinement of this embodiment, a pre-formed spacer 760 is provided to produce the necessary antero-posterior force vector. As discussed above, in the case of the custom made knee orthosis 100, the medial side attachment 204 (FIGS. 1–2) were located further forward on the lower support shell 104 which, in combination with positioning suspension strap 116 on the inside of the tibial strut links 108, provided for an antero-posterior directed force. Since the off-the-shelf knee orthosis 700 lacks a lower support shell to which the suspension strap 716 can be so attached, the spacer 760 is used as an alternative means for achieving this antero-posterior directed force in conjunction with positioning of the suspension strap 716 on the inner sides of the tibial strut links 708.

That is, in the present embodiment, the pre-formed spacer 760, as shown, is positioned on the inner side of suspension strap 716 (i.e., the side contacting the wearer's leg) and directly adjacent the inner side of the medial tibial strut 708. The pre-formed spacer 760 can be made of any sponge-like material that is comfortable to the wearer, and it may be permanently connected, or as shown in the present embodiment, detachably connected to suspension strap 716 using a conventional Velcro® type hook and loop fabric attachment means. The main advantage of the pre-formed spacer 760 is that it provides exceptional suspension and support by converting the normal line of force of the suspension strap 716 from being directed across, or horizontal, to the wearer's leg, to an antero-posterior directed force. This change of force greatly diminishes the possibility that the suspension strap 716 will displace down over the calf because, now, the line of force is directly against the calf, and the suspension strap 716 cannot slip down onto the fibular neck, as can be seen in FIG. 5. Furthermore, if one pre-formed spacer 760 is inadequate to provide the necessary antero-posterior directed force, then an additional pre-formed spacer can be attached to the outer side of the suspension strap 716 between the strap and the inner side of tibial strut 708. Additionally, while the spacer 760 is shown only on the medial side, it may be necessary for some wearer's to also provide a spacer 760 at the lateral side.

In addition, due to the suspension strap 716 having a line of force directly against the calf of the wearer, a cushioning spacer 762 may be used to provide comfort for the user without decreasing the contact area of the suspension strap relative to the wearer's leg. This cushioning spacer 762 may be made of a similar material to the pre-formed spacer 760, and can be permanently attached to the suspension strap 716, or detachably connected using a Velcro® type hook and loop fabric attachment means.

It is noted that, while the pre-formed spacer 760 and the cushioning spacer 762 have been described in conjunction with the off-the-shelf knee orthosis 700, they may also be used in conjunction with the custom made knee orthosis 100 described in conjunction with FIG. 1.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

We claim:

1. A knee orthosis comprising:

an upper support portion including an upper frontal cross member connecting a lateral femoral strut with a medial femoral strut;

a lower support portion including a lower frontal cross member connecting a lateral tibial strut with a medial tibial strut;

a lateral joint mechanism connecting said lateral femoral strut with said lateral tibial strut, and a medial joint mechanism connecting said medial femoral strut with said medial tibial strut for controlling bending movement of a wearer's leg; and means for securing the knee orthosis to a wearer's leg; wherein said means for securing includes a suspension strap having an inelastic band portion extending between said tibial struts passing posteriorly of the wearer's leg in use said suspension strap being connected to said lateral tibial strut at a point which is higher than a point of connection of said suspension strap to said medial tibial strut.

2. The knee orthosis of claim 1, wherein said suspension strap further comprises connecting means for connecting said suspension strap to an inner facing of said lower frontal cross member.

3. The knee orthosis of claim 2, further comprising a pre-formed spacer means positioned adjacent said band portion for causing the suspension strap to exert an antero-posterior directed force relative to the wearer's leg.

4. The knee orthosis of claim 3, wherein said pre-formed spacer means is detachably connected to said band portion using hook and loop fabric attachment means.

5. The knee orthosis of claim 4, wherein said pre-formed spacer means is positioned directly adjacent each of said tibial struts.

6. The knee orthosis of claim 2, wherein each of said upper cross member and said lower cross member is formed by a support shell which conforms to a natural shape of the wearer's leg, having been pre-molded thereto.

7. The knee orthosis device of claim 1, wherein said suspension strap further comprises a cushioning means detachably connected to said band portion using hook and loop fabric attachment means; wherein said cushioning means provides cushioning between said suspension strap and the wearer's leg.

8. The knee orthosis device of claim 1, further comprising a connecting means for attaching said suspension strap to said lower support portion; wherein said band portion of the said suspension strap traverses from inner sides of said tibial struts to outer sides of said tibial struts; and wherein said connecting means connects said band portion to said lower support portion.

9. The knee orthosis of claim 1 wherein said suspension strap is set at an angle relative to the tibial struts which positions the suspension strap for preventing compression of a fibular neck of a calf of the wearer's leg.

10. A knee orthosis comprising:

an upper support portion including an upper frontal cross member connecting a lateral femoral strut with a medial femoral strut;

a lower support portion including a lower frontal cross member connecting a lateral tibial strut with a medial tibial strut;

a lateral joint mechanism connecting said lateral femoral strut with said lateral tibial strut, and a medial joint mechanism connecting said medial femoral strut with said medial tibial strut for controlling bending movement of a wearer's leg; and means for securing the knee orthosis to a wearer's leg, said means for securing comprising a suspension strap having a band portion connected to each of said tibial and traversing inner sides of the tibial struts between points of connection of the band to the tibial struts; and a pre-formed spacer means positioned adjacent said band portion for causing the suspension strap to exert an antero-posterior directed force relative to the person's leg.

11. The knee orthosis of claim 10, wherein said pre-formed spacer means is detachably connected to said band portion by a hook and loop fabric attachment means.

12. The knee orthosis of claim 11, wherein said pre-formed spacer means is positioned directly adjacent each said tibial strut.

13. The knee orthosis of claim 10, wherein said suspension strap further comprises a cushioning means detachably connected to said band portion by a hook and loop fabric attachment means; and wherein said cushioning means provides cushioning between said suspension strap and the wearer's leg.

14. The knee orthosis of claim 10, further comprising connecting means for attaching the band portion of said suspension strap to said lower support portion with said band portion running from an outer side of each tibial strut to an inner side thereof.

15. The knee orthosis of claim 10, wherein said suspension strap is set at an angle relative to the tibial struts which positions the suspension strap for avoiding compression of a fibular neck of a calf of the wearer's leg.

* * * * *